(12) United States Patent
Barstow

(10) Patent No.: US 6,267,591 B1
(45) Date of Patent: Jul. 31, 2001

(54) DENTAL PROP, THROAT DAM AND RETRACTOR

(76) Inventor: Ricky A. Barstow, 2181 Bloomfield Rd., Cambridge, OH (US) 43725

( * ) Notice: Subject to any disclaimer, the term of this patent is extended or adjusted under 35 U.S.C. 154(b) by 0 days.

(21) Appl. No.: 09/551,637

(22) Filed: Apr. 18, 2000

(51) Int. Cl.$^7$ ................................................. A61C 17/06
(52) U.S. Cl. ............................................. 433/93; 433/140
(58) Field of Search .................... 433/140, 93; 128/859, 128/860; 600/238, 239, 242

(56) References Cited

U.S. PATENT DOCUMENTS

| | | | |
|---|---|---|---|
| 692,281 | * 2/1902 | Hare | 433/93 |
| 2,023,288 | 12/1935 | Pickett | 128/12 |
| 2,220,674 | 11/1940 | Bloombeart | 128/12 |
| 2,831,480 | * 4/1958 | Milano | 433/93 |
| 3,090,122 | 5/1963 | Erickson | 32/33 |
| 3,638,013 | 1/1972 | Keller | 240/41.15 |
| 3,924,333 | * 12/1975 | Erickson | 433/93 |
| 4,002,162 | 1/1977 | Weisser | 128/17 |
| 4,019,255 | 4/1977 | Cohen et al. | 32/33 |
| 4,024,642 | * 5/1977 | Zorovich | 433/140 |
| 4,053,984 | 10/1977 | Moss | 32/33 |
| 4,148,308 | 4/1979 | Sayer | 128/15 |
| 4,167,814 | 9/1979 | Schubert | 32/33 |
| 4,259,067 | 3/1981 | Nelson | 433/93 |
| 4,261,697 | 4/1981 | Newitter | 433/137 |
| 4,511,329 | 4/1985 | Diamond | 433/31 |
| 4,521,185 | 6/1985 | Cohen | 433/31 |
| 4,616,633 | 10/1986 | Vargas Garcia | 128/20 |
| 4,887,965 | 12/1989 | Fox | 433/140 |
| 4,889,491 | 12/1989 | Krygier et al. | 433/136 |
| 4,992,046 | 2/1991 | Sharp | 433/93 |
| 5,009,595 | 4/1991 | Osborn | 433/140 |
| 5,097,820 | 3/1992 | Shulman et al. | 128/17 |
| 5,115,799 | 5/1992 | McGann | 128/12 |
| 5,205,733 | 4/1993 | Scheels | 433/1 |
| 5,244,386 | 9/1993 | Angelo, Jr. | 433/72 |
| 5,462,435 | 10/1995 | Young | 433/140 |
| 5,466,153 | 11/1995 | Poindexter | 433/140 |
| 5,588,836 | 12/1996 | Landis et al. | 433/93 |
| 5,664,946 | 9/1997 | Bedi | 433/140 |
| 5,735,691 | 4/1998 | Fetter | 433/140 |
| 5,873,718 | 2/1999 | Sullivan | 433/93 |
| 5,890,899 | 4/1999 | Sclafani | 433/140 |
| 5,924,866 | 7/1999 | Eldreth | 433/140 |
| 6,022,214 | * 2/2000 | Hirsch et al. | 433/140 |

FOREIGN PATENT DOCUMENTS

1078867 * 11/1954 (FR) ................................. 433/140

* cited by examiner

*Primary Examiner*—Todd E. Manahan
(74) *Attorney, Agent, or Firm*—Renner, Kenner, Greive, Bobak, Taylor & Weber

(57) ABSTRACT

A dental device (10) includes a tongue-retracting surface (14) and a throat dam (15, 16) adapted to be positioned in the mouth of a patient. Integral lip-retracting surfaces (17) and a grip portion (18) are connected to the tongue-retracting surface (14) and throat dam (15, 16) by a prop portion (12) which preferably have angled biting surfaces (19) adapted to be engaged by the teeth of the patient. An expandable throat barrier net (23) may be attached to a portion of the throat dam (15). An evacuation system (30) may be provided to remove fluids from the mouth. The biting surfaces (19) may be provided with a pad (21) or a thermoplastic material (22) for the comfort of the patient. A reflective material (27) may be attached to the tongue-retracting surface (14) and a fiber optic rod (28) may be carried by the tongue-retracting surface (14) to assist in illuminating the oral cavity of the patient.

18 Claims, 4 Drawing Sheets

DENTAL PROP, THROAT DAM AND RETRACTOR

TECHNICAL FIELD

The present invention generally relates to an improved dental device which includes a dental prop with an integrated throat dam and tongue retractor. More particularly, the present invention relates to a dental device which includes a dental prop, tongue retractor, lip retractor and throat dam with an integrated suction device to aid in dental and oral surgical procedures.

BACKGROUND ART

Dental props, tongue retractors (positioners), lip and cheek retractors and saliva evacuation devices are commonly used in dental and oral surgery practice. Such devices facilitate dental and oral surgery procedures by improving visibility and increasing the available working space within a patient's mouth, and by removing saliva, blood, debris and the like from the patient's mouth which would otherwise accumulate and interfere with dental operations and generally increase patient discomfort.

Dental props are devices which are inserted into the patient's mouth between upper and lower teeth to keep the mouth opened in a fixed position while the dentist is working in the patient's mouth. Normally the teeth on one side of the mouth engage the dental prop while the dentist is working on the teeth on the opposite side of the mouth. Dental props are desirable, particularly in order to enhance the efficiency of the dentist, so the dentist does not have to continually remind the patient to keep the mouth open at a certain angle and also so that the dentist does not have to be concerned with the patient inadvertently biting his or her fingers or the dental instruments. Props also act as comfortable rests for the patient. In the past, various appliances have been used to isolate or open parts of the mouth to facilitate the performing of dental services. In addition to dental props, expansion forceps have been used to hold the patient's jaws open.

Another problem encountered during dental procedures is that the oral cavity is constantly being filled with body fluids, such as saliva. If these body fluids are not removed, they may adversely effect many of the dental procedures that require a dry field for success. Also, a buildup of saliva or body fluid in the mouth has a negative impact on the patient's comfort. The proximity of the oral soft tissues, such as the tongue, cheek and lip, to the field of work may make it difficult to perform those dental procedures also requiring a dry field. Therefore, the success of many operative dental procedures requires the removal of body fluids and soft tissues from the field of work.

Saliva removal is further necessitated because dental procedures frequently involve substances, such as mercury amalgam particles, which are unhealthy to ingest and would otherwise be swallowed by a patient if not removed by suction. Several devices are known in the dental and oral surgery professions for positioning a patient's mouth and tongue during treatment and/or removing saliva and debris therefrom. Most of the known devices do not contain an integral saliva evacuation device. As a result, an additional tube or hook must be inserted into the oral cavity which further impairs viewing and makes the proper and effective positioning of the evacuation device difficult and cumbersome for the dental professional who, in this regard, often requires the help of a dental assistant.

An additional area of concern is that, in dentistry, it has been the practice to use a dental lamp in combination with a dental mouth mirror to assist viewing while performing work in the oral cavity. The dental lamp is a light source providing a large beam of light which may be focused in the general area of a patient's mouth. Thereafter, a dental mirror is used to indirectly view inaccessible areas of the mouth, or to retract the tongue or cheek in order to view an area directly. Such technique has not been entirely satisfactory. A dentist's hands and/or instruments often shade the area which is being viewed, thereby requiring the dentist to assume an awkward position so as not to shade the area being viewed. During an oral examination or dental cleaning, where each tooth and various other structures are observed and manipulated, the dental lamp must constantly be adjusted, resulting in considerable time loss and frustration.

It is also known in the art to use lip and/or cheek spreaders or retractors. By retracting the cheek or lips the dental professional is able to increase the viewable area of the oral cavity.

Another impediment to the practice of dentistry relates to the human tongue. The tongue extends from an elevated arc area near the throat toward the tongue tip at the anterior aspect of the mouth. The arc area of the tongue must be depressed to obtain a good view of the mouth, and control of the tongue has proven to be problematic in both conscious and unconscious patients. In conscious patients the tongue can become fatigued when the patient attempts to hold the tongue away from the area of concern for extended periods of time. Additionally, the tongue is involved in several involuntary responses such as swallowing or the gag reflex. The unconscious patient is simply unable to keep the tongue away from the area where the dental professional is working and is also susceptible to all of the same involuntary actions as the conscious patient.

If the tongue moves into the area of the oral cavity where the dental professional is working, several problems can occur. Not only might the dental professional's view be impaired, but also the tongue may be injured by a dental instrument. It is therefore important to keep control of the tongue's position in the mouth.

Several appliances are know in the art which attempt to solve one or more of the above-mentioned problems. One such appliance which is used for isolating parts of the mouth is the rubber dam which consists of a flexible piece of material having holes disposed therein to permit placement down over the teeth into surface contact with the gums so that the teeth protrude through the holes in the rubber dam. The rubber dam does not have a flexible frame having cheek and tongue deflectors attached thereto or a provision for saliva removal.

There are also several known appliances which serve as dental props. One such device consists of an oval shaped frame having lip deflectors attached thereto. It does not have provision for saliva ejection or tongue deflection. Moreover, it may only be used to isolate the anterior teeth.

Another dental prop is shown in U.S. Pat. No. 2,023,288 which is adjustable by means of a wedge having beveled notches. The wedge is forced between opposed jaw engaging members to open the patient's mouth. The beveled notches engage a lug on one of the jaw engaging members to secure the wedge in place. However, the use of notches and a lug in this dental prop provides for only incremental adjustment. Also, the beveled notches provide for smooth adjustment only when the wedge is inserted further into the mouth. This means that, were the patient's mouth to be closed only slightly, the wedge has to be completely retracted. The fact that the patient first has to open his mouth in order for the wedge to be removed and repositioned means that the dental procedure has to be interrupted, thereby prolonging patient discomfort. Moreover, this dental prop includes two pieces. This poses the risk that one of the pieces may be lost by the dentist or swallowed by the patient. Furthermore, the wedge and the jaw engaging members form a barrier on one side of the patient's mouth which obstructs the view of the working area of the mouth for an assistant, where assistance is required during the dental procedure.

U.S. Pat. No. 3,090,122 discloses a device which is molded of a waterproof or liquid impervious flexible material such as rubber or plastic. The device has a central depressed portion in which saliva pools and is collected. The marginal edges of the device are adapted to provide a sealing engagement with the roof and floor of the mouth, with the device being between the patient's teeth and tongue. The patient may experience a gagging sensation with the device due to the sealing engagement of the device with the roof of the mouth. The saliva and debris are collected through a pair of apertures positioned basically in the center of the device. With the patient's head typically tilted backward, saliva and debris tends to pool or collect along the floor of the mouth or lower edge portion of the dental device. With the saliva and debris collecting apertures disposed somewhat centrally on the device, saliva removal may not necessarily be very efficient. Moreover, this device is a relatively high cost item, and as with the rubber dam, must be effectively sterilized prior to each use thereof. Finally, when the dentist uses an auxiliary vacuum evacuator, rubber or plastic material tends to be drawn against the evacuator blocking the opening.

U.S. Pat. No. 2,220,674 discloses a device with a cheek-engaging convex portion having a pair of spaced diverging trough portions that form a U-shaped trough section on which the teeth rest. Devices fitting this general description continue to be sold and used. These devices are simple in design and relatively inexpensive; however, if the patient is unable or unwilling to cooperate due to age, mental disability, or response to medication, the dental practitioner or an assistant will have difficulty getting the device to remain in place. Attempts to hold the device in place may result in impaired visibility of, and access to, the mouth. Furthermore, the person holding the device in place is subject to injury from biting or contact with devices used by the dental practitioner.

Regarding lighting and mirror appliances, U.S. Pat. No. 3,638,013 discloses a fiber optic lighting system having a fiber optic cable which transmits light from a distant light source to illuminate the area of the mouth in which an instrument is being used. Unfortunately, prior art combinations of a fiber optic cable with a dental mouth mirror have proven to be unacceptable. Such combinations have been cumbersome and significantly limited the maneuverability of the mouth mirror. Moreover, such combinations are not readily transportable and can only be used in suitably equipped dental operatory.

None of the above patents provide for suctioning the soft palate region of the mouth behind the dental appliance. Nor do they disclose illumination of the mouth cavity at selected sites. Usually the dental assistant must suction and evacuate the mouth with a hand-held suction device. The mouth illumination devices as previously discussed are provided at a fixed location in the mouth and thus do not provide for changeable illumination of certain portions of the mouth cavity.

The prior art also has long testified to the need for a dental device which would serve to readily withdraw or expand the lips and cheeks and retract the tongue from their normal position in order to facilitate both a visual and physical access to the teeth as well as to other anatomical areas such as the gingivae surrounding the teeth and the palate and throat, and simultaneously aid in maintaining a clean, dry field of operation without the assistance of an auxiliary person.

DISCLOSURE OF THE INVENTION

It is thus an object of the present invention to provide a device which serves as a dental prop with an integrated throat dam and tongue and lip retractor.

It is another object of the present invention to provide a device, as above, which is inexpensive to manufacture and which therefore could be disposable but yet be autoclavable for further usage.

It is a further object of the present invention to provide a device, as above, which readily exposes the area of concern in the oral cavity allowing the dental professional to have total visual and physical access to such area.

It is an additional object of the present invention to provide a device, as above, which provides a dry, fluid-free area in the oral cavity with access thereto not being impaired by additional tubing or the like.

It is still another object of the present invention to provide a device, as above, which precludes interference of the tongue in the area of the oral cavity being addressed by the dental professional.

It is yet another object of the present invention to provide a device, as above, in which the throat is protected from the ingestion of any debris in the mouth.

It is a still further object of the present invention to provide a device, as above, in which the area of the mouth being worked upon can be better illuminated.

It is an additional object of the present invention to provide a device, as above, which helps to eliminate the need for a dental assistant when the dentist is working in the oral cavity of a patient.

It is a further object of the present invention to provide a device, as above, in which the prop opening can be readily varied from device to device so as to accommodate various sizes of jaw openings so that the patient may maintain a comfortable grip on the device.

These and other objects of the present invention, as well as the advantages thereof over existing prior art dental devices, which will become apparent from the description to follow, are accomplished by the improvements hereinafter described and claimed.

In general, a dental device adapted to be placed in the mouth of the patient includes an intra-oral portion and an extra-oral portion. The intra-oral portion includes a tongue retractor and a throat dam. The extra-oral portion includes lip-retracting surfaces and a grip portion. The intra-oral and extra-oral portions are integrally connected by a prop portion which has opposed biting surfaces adapted to be engaged by the teeth of the patient.

In accordance with another aspect of the present invention, the device includes a lip retractor and a tongue retractor integrally connected by a prop portion. The prop portion has opposed biting surfaces which converge toward each other from the tongue retractor to the lip retractor to present angled surfaces which accommodate the hinge action of an open jaw when engaged by the teeth of the patient.

A preferred exemplary dental device incorporating the concepts of the present invention is shown by way of example in the accompanying drawings without attempting to show all the various forms and modifications in which the invention might be embodied, the invention being measured by the appended claims and not by the details of the specification.

PREFERRED EMBODIMENTS FOR CARRYING OUT THE INVENTION

Figure 1:
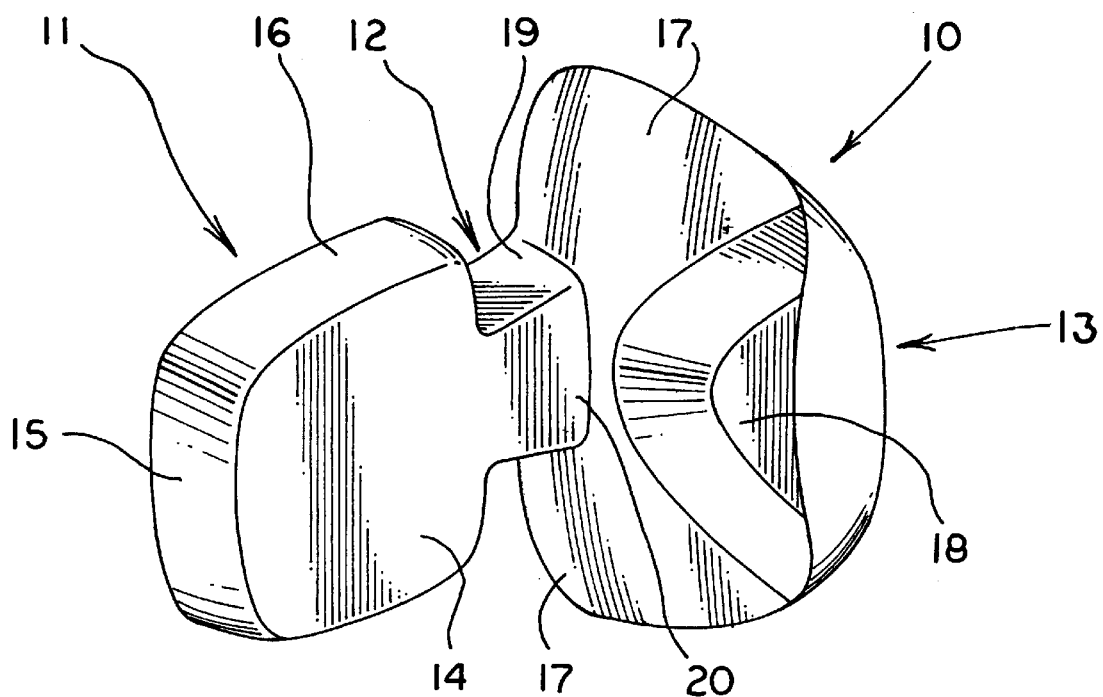
FIG. 1 is a perspective view of a dental device made in accordance with the present invention.
Figure 2:
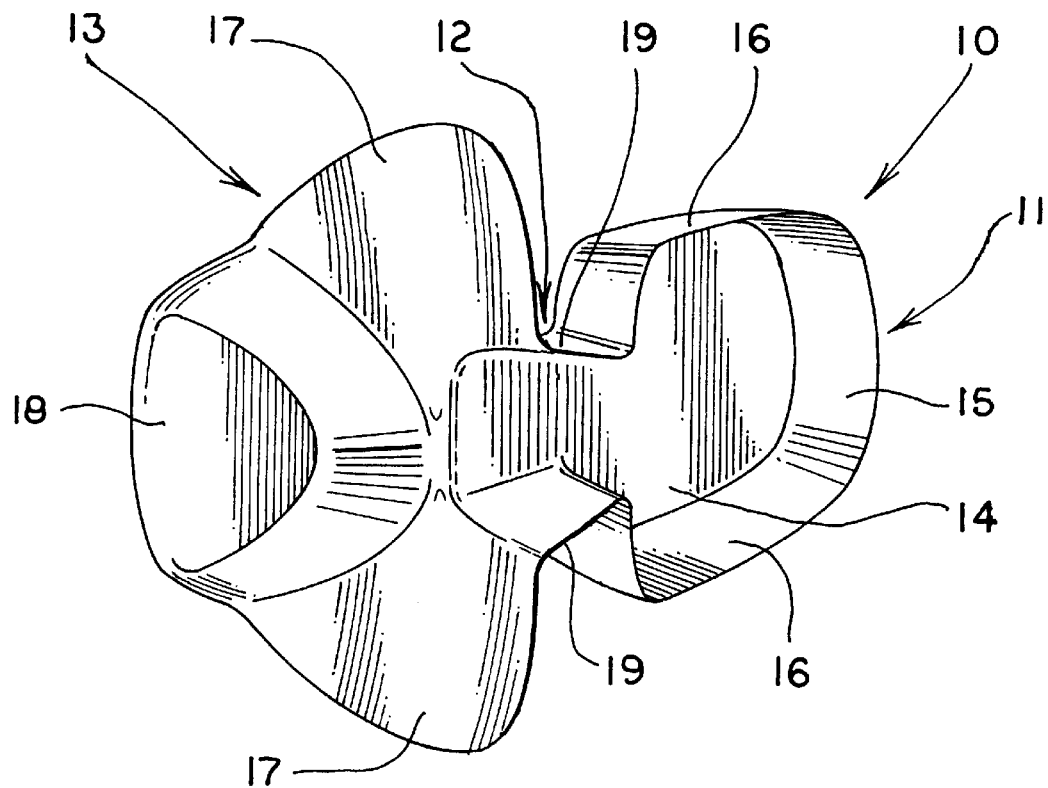
FIG. 2 is a perspective view of the other side of the dental device shown in FIG. 1.

A dental device for isolating a portion of the mandibular and maxillary arch is adapted to be placed in the mouth in a substantially vertical orientation generally between the upper and lower teeth, and is generally indicated by the numeral 10. Dental device 10 includes an intra-oral portion, generally indicated by the numeral 11, connected by a prop portion, generally indicated by the numeral 12, to an extra-oral portion, generally indicated by the numeral 13. Dental device 10 may be formed out of any suitable thermoplastic material.

Intra-oral portion 11 is preferably generally cup-shaped having a tongue-retracting surface 14 which, when device 10 is placed in the mouth of a patient, pushes the tongue to the side to clear the area being worked on by the dental professional. A u-nshaped flange having a base portion 15 with side surfaces 16 extending therefrom, extends outwardly from surface 14. When in the mouth, surface 14 is facing the patient's cheek. As will hereinafter be described in more detail, this u-nshaped flange, and in particular base portion 15, acts as a throat dam.

Figure 3:
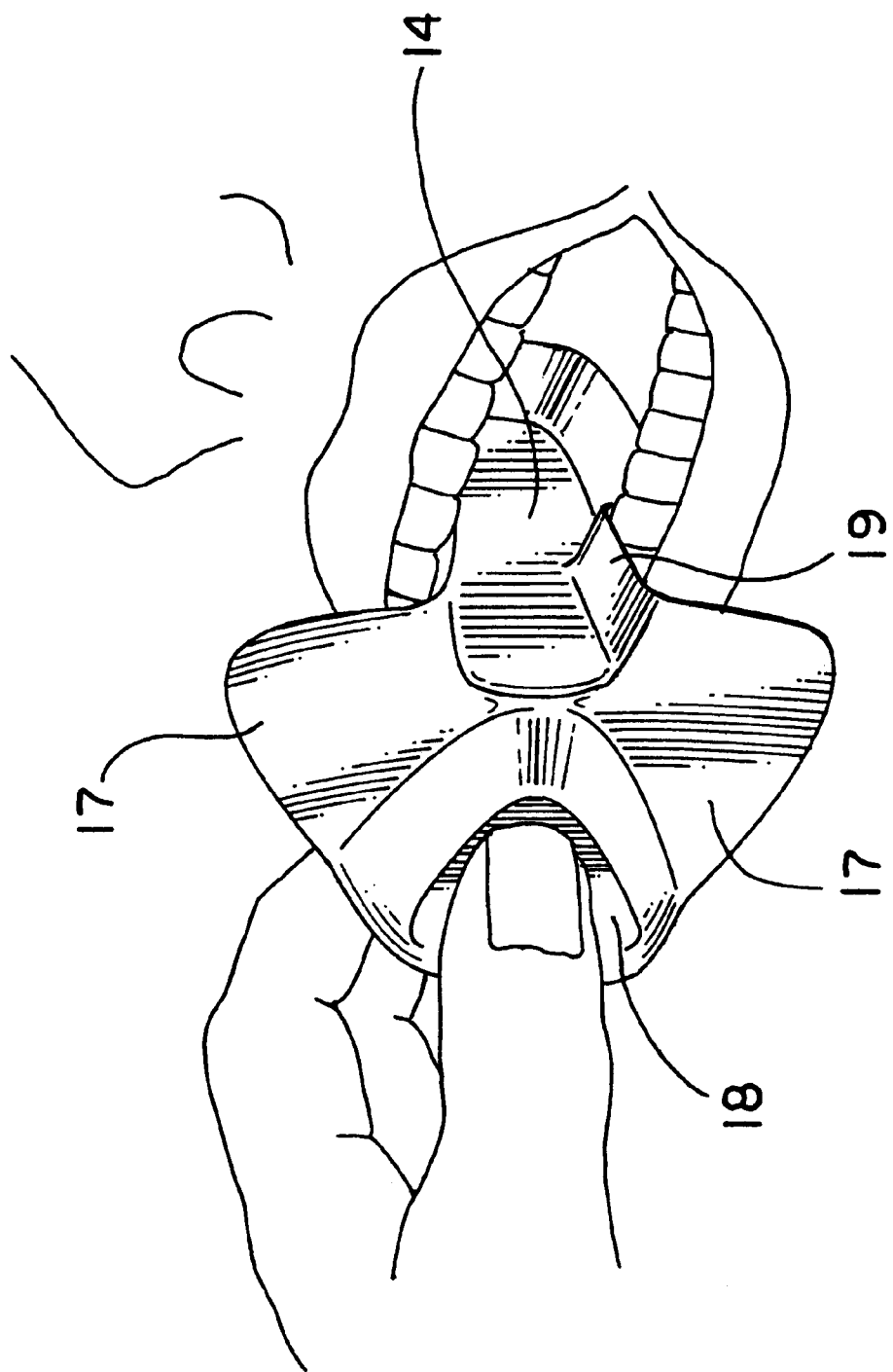
FIG. 3 is a perspective view depicting the dental device of FIGS. 1 and 2 being deployed into the mouth of a patient.

Extra-oral portion 13 includes arcuate lip-retracting surfaces 17 with a grip portion 18 formed integrally therewith. As shown in FIG. 3, to insert device 10 into the mouth of the patient, the dental professional need only grasp portion 18 with the thumb and index finger and insert device 10 with surface 14 horizontally oriented under the tongue. Then device 10 may be rotated ninety degrees to the position shown in FIG. 3. By such action, surface 14 pushes the tongue to the side. Moreover, as device 10 is inserted, the lips of the patient are retracted, or otherwise pushed aside, by surfaces 17.

Prop portion 12 maintains the mouth of the patient open at a fixed position. As such, it includes upper and lower opposed biting surfaces 19 interconnected by a tab extension 20 of tongue-retracting surface 14. Biting surfaces 19 thus extend between intra-oral portion 11 and lip-retracting surfaces 17 of extra-oral portion 13, and are adapted to be engaged by a biting force of a patient. As shown, biting surfaces 19 preferably converge slightly toward each other as they extend from extra-oral portion 13 to intra-oral portion 11. This angled nature of biting surfaces 17 accounts from the angle created by the hinge axis of the jaw joint, and thus provides the patient with a degree of comfort when biting down on surfaces 19, as well as improving an even contact of the teeth on surfaces 17 from front to back.

Figure 4:
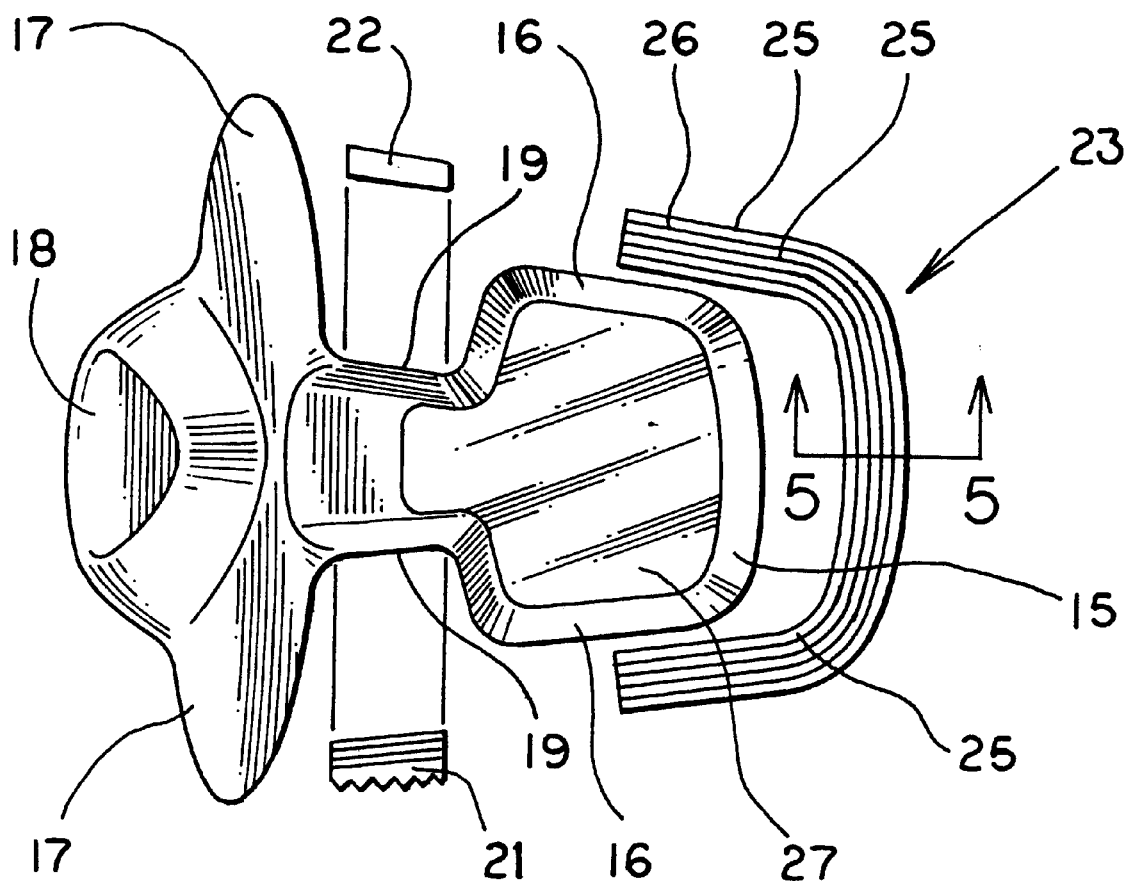
FIG. 4 is an exploded elevational view of the dental device depicting some optional features to be used in conjunction therewith.

Of course, it should be appreciated that dental device 10 may be provided in many sizes dependent on the size of the mouth of the patient. But even when the appropriately sized device 10 is selected, device 10 may be optionally provided with accessories rendering it more comfortable for the patient. For example, as shown in FIG. 4, an adhesive-backed elastomeric or rubber pad 21 may be positioned on the angled biting surfaces 19 of prop portion 12. Rubber pad 21 may be provided with a serrated surface, as shown in FIG. 4, and it increases the ability of the teeth to grip the biting surface 19, with the chance of dental device 10 slipping thereby being decreased. The addition of rubber pad 21 also increases patient comfort and provides a more stable gripping of prop portion 12. In another contemplated embodiment shown in FIG. 4, a thermoplastic material 22 is prepared by heating and affixing a warmed, and thus softened, thermoplastic material 22 to biting surfaces 19. While thermoplastic material 22 is still malleable, it is impressed by the teeth and allowed to cool and harden. This molding process creates a customized and intimate contact between the teeth and biting surface 19 which thus reduces slippage and increases patient comfort.

Figure 5:
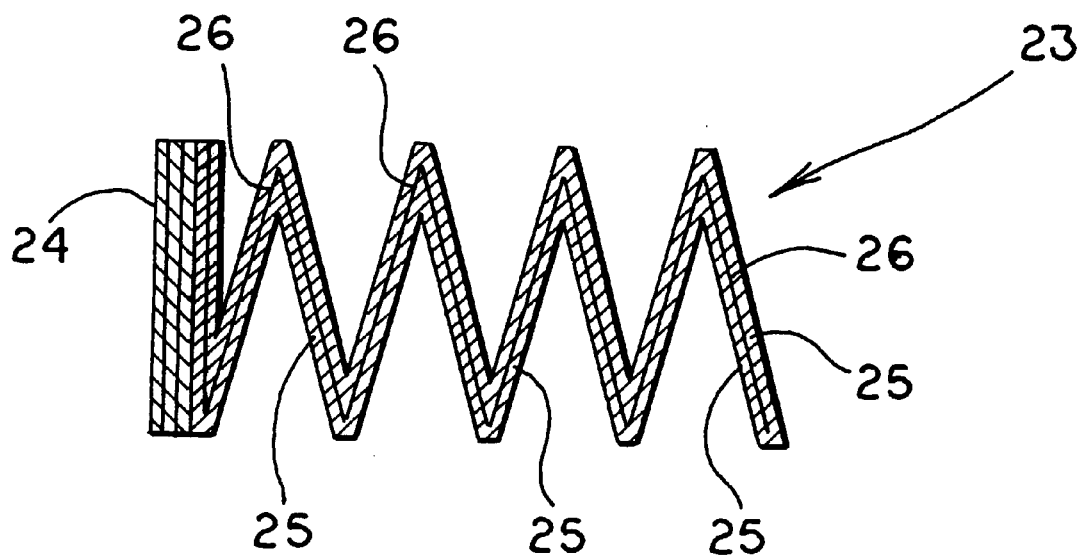
FIG. 5 is a sectional view taken substantially along line 5—5 of FIG. 4.

In order to more effectively seal the throat from swallowing or ingesting of any debris in the mouth, device 10 may also be provided with an expandable throat barrier net generally indicated by the numeral 23 and schematically shown in FIG. 4. Expandable net 23 may be attached to base portion 15 of the u-nshaped flange, throat dam, as by a double-sided adhesive tape 24. As shown in FIGS. 4 and 5, net 23 may be made of thin sheets 25 of a plastic material which sandwich a "dead soft" chicken wire-like mesh 26 therebetween. Net 23 may be folded together in an accordion-like fashion and may be expanded to fill the space between the throat dam and the palate and other oral tissues. Expandable net 23 may thus be manipulated by a small dental instrument to conform to the desired configuration and protect the throat from debris, mesh 26 maintaining that configuration once it is established.

Figure 6:
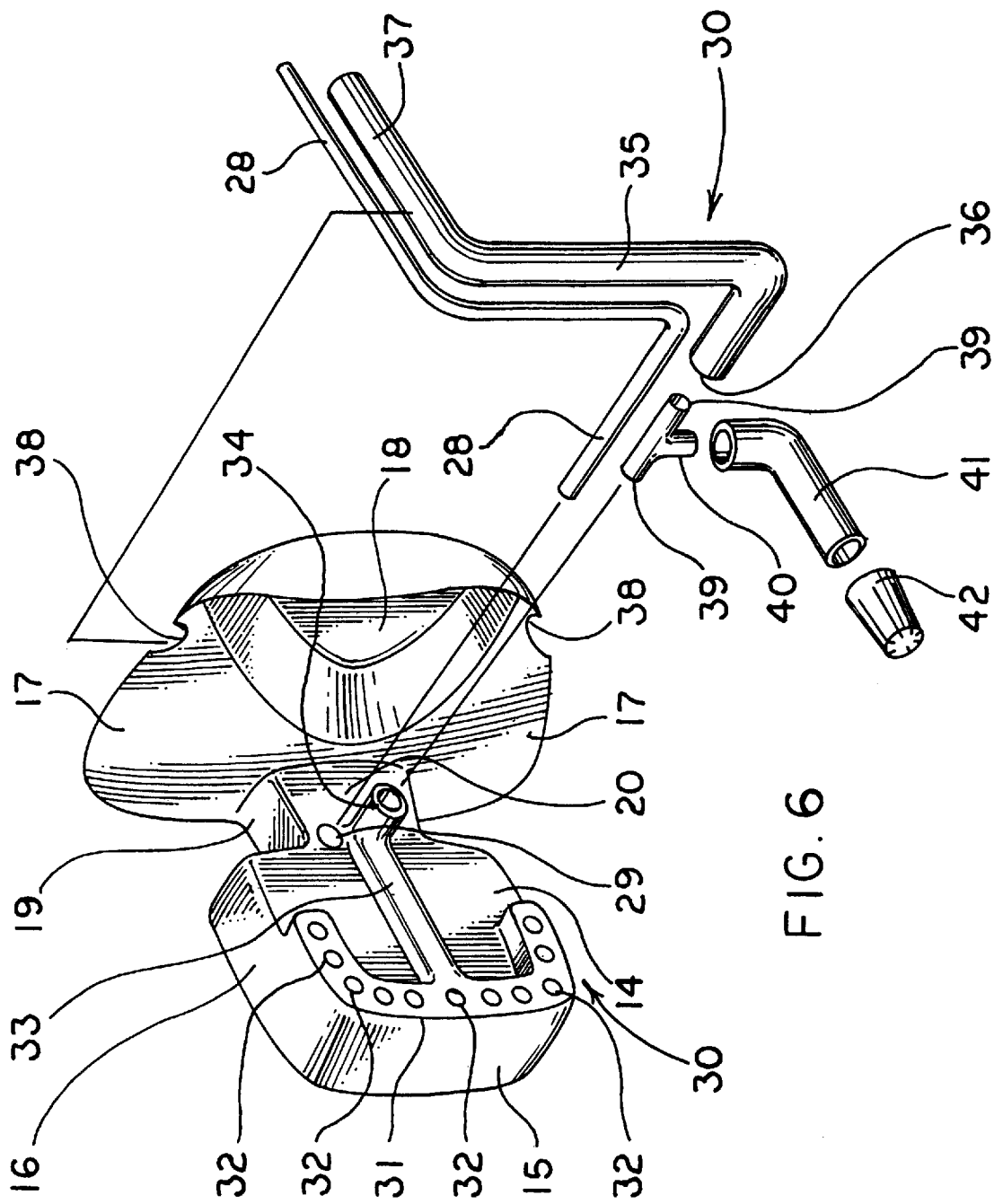
FIG. 6 is an exploded perspective view depicting the dental device with some optional features to be used in conjunction therewith.

In order to assist in the illumination of the area being worked on by the dental professional, as shown in FIG. 4, the side of tongue retraction surface 14 facing the teeth may be provided with a reflective material 27. When dental device 10 is used so that the jaw is propped open by prop portion 12, the lips and cheeks are retracted by retracting surfaces 17, and the tongue-retracting surface 14 keeps the tongue out of the way, a light shining on reflective material 27 will be reflected toward the area being worked upon by the dental professional. Alternatively, or additionally, as schematically shown in FIG. 6, dental device 10 may be provided with a flexible fiber optic rod 28. One end of rod 28 may be received through an aperture 29 formed through tab 20 to communicate with a light source. Rod 28 may then be bent or manipulated so that the other end thereof may emit light as directed by the dental professional.

In another embodiment, dental device 10 may be provided with an integrated saliva or fluid evacuation system generally indicated by the numeral 30 and shown in FIG. 6. A portion of evacuation system 30 is molded directly into dental device 10. As such, intra-oral portion 11 is provided with channel 31 formed at the orally-inner peripheral edge of the u-nshaped flange thereof. Channel 31 is provided with a series of perforations 32, which extend through intra-oral portion 11 so that perforations 33 communicate with the oral cavity on both sides of intra-oral portion 11. Channel 31 communicates with one end of another channel 33 formed on tongue retracting surface 14. A hub 34 is formed at the other end of channel 33 and extends orally inwardly from surface 14 when device 10 is in the mouth of a patient.

Evacuation system 30 also includes a flexible evacuation tube 35 having one end 36 connected to hub 34 and its other end 37 connected to a suction source as is commonly found in a dental office. Tube 35 may be conveniently maintained in a position out of the way of the dental professional by being received in the top one of two opposed notches 38 formed in surfaces 17 of device 10, there being two notches 38 because device 10 is merely flipped over when working on the other side of the mouth. As a result, saliva and other fluids are drawn in through perforations 32, through channel 33 and into tube 35 for evacuation from the mouth.

In order to evacuate fluids from the base of the mouth, evacuation system 30 may be provided with a secondary system which includes a t-tube 40 having branches 39 received between tube 35 and hub 34. A flexible tube 41 has one end connected to t-tube 40 and may be positioned by the dental professional so that its other end is approximately positioned at the bottom of the mouth of the patient. This other end of tube 41 may be provided with a strainer 42 to prevent tube 41 from being clogged with debris, soft tissue, or the like.

In light of the foregoing, it should thus be evident that a dental device 10 constructed as described herein substantially improves the art and otherwise accomplishes the objects of the present invention.

What is claimed is:

1. A dental device adapted to be placed in the mouth of a patient comprising an intra-oral portion including a tongue retractor and a throat dam, said throat dam being in the form of a u-shaped flange that extends away from the cheek of the patient when the dental device is placed in the patient's mouth, an extra-oral portion including lip-retracting surfaces and a grip portion, and a prop portion integrally connecting said intra-oral portion and said extra-oral portion, said prop portion having opposed biting surfaces adapted to be engaged by the teeth of the patient.

2. A dental device according to claim 1 wherein said opposed biting surfaces converge toward each other from said extra-oral portion to said intra-oral portion.

3. A dental device according to claim 1 further comprising means positioned on said biting surface to enhance the engagement by the teeth of the patient.

4. A dental device according to claim 3 wherein said means includes an adhesive-backed elastomeric pad.

5. A dental device according to claim 3 wherein said means includes a thermoplastic material.

6. A dental device according to claim 1 wherein said tongue retractor is provided with a reflective surface.

7. A dental device according to claim 1 further comprising a fiber optic rod carried by said tongue retractor.

8. A dental device according to claim 1 further comprising a system carried by said intra-oral portion adapted to remove fluids from the mouth.

9. A dental device according to claim 8 wherein said system includes a channel formed in said intra-oral portion, said channel having perforations communicating with the fluids in the mouth.

10. A dental device according to claim 9 herein said system includes a tube communicating with said channel and adapted to be attached to a suction source.

11. A dental device according to claim 10 wherein said lip-retracting surfaces are provided with at least one notch to engage said tube.

12. A dental device according to claim 10 wherein said system includes a second tube communicating with said first tube, said second tube being positionable to communicate with fluids in the bottom of the mouth.

13. A dental device according to claim 12 wherein said system includes a strainer connected to said second tube.

14. A dental device adapted to be placed in the mouth of a patient comprising an intra-oral portion including a tongue retractor and a throat dam, an extra-oral portion including lip-retracting surfaces and a grip portion, a prop portion integrally connecting said intra-oral portion and said extra-oral portion, said prop portion having opposed biting surfaces adapted to be engaged by the teeth of the patient, and a throat barrier adapted to be attached to said throat dam.

15. A dental device according to claim 14 wherein said throat barrier includes an embedded corrugated material rendering said throat barrier expandable.

16. A dental device adapted to be placed in the mouth of a patient comprising a lip retractor, a tongue retractor, a throat dam in the form of a u-shaped flange extending from said tongue retractor away from the cheek of a patient when the device is placed in a patient's mouth, and a prop portion integrally connecting said lip retractor and said tongue retractor, said prop portion having opposed biting surfaces which converge toward each other from said tongue retractor to said lip retractor to present angled surfaces which accommodate the hinge action of an open jaw when said surfaces are engaged by the teeth of the patient.

17. A device according to claim 16 further comprising a grip portion integrally formed with said lip retractor.

18. A device according to claim 16 further comprising a throat dam integrally formed with said tongue retractor.

* * * * *